(12) United States Patent
Erko et al.

(10) Patent No.: US 9,417,341 B2
(45) Date of Patent: Aug. 16, 2016

(54) DEVICE AND METHOD FOR DETERMINING THE ENERGETIC COMPOSITION OF ELECTROMAGNETIC WAVES

(71) Applicants: IfG—Institute for Scientific Instruments GmbH, Berlin (DE); Helmholtz-Zentrum Berlin fur Materialien und Energie GmbH, Berlin (DE)

(72) Inventors: Alexei Erko, Berlin (DE); Norbert Langhoff, Berlin (DE); Aniuar Bjeoumikhov, Berlin (DE)

(73) Assignees: IfG—Institute for Scientific Instruments GmbH, Berlin (DE); Helmholtz-Zentrum Berlin fuer Materialien und Energie GmbH, Berlin (DE)

( * ) Notice: Subject to any disclaimer, the term of this patent is extended or adjusted under 35 U.S.C. 154(b) by 170 days.

(21) Appl. No.: 14/253,943

(22) Filed: Apr. 16, 2014

(65) Prior Publication Data

US 2014/0314207 A1    Oct. 23, 2014

(30) Foreign Application Priority Data

Apr. 19, 2013  (DE) .......................... 10 2013 207 160

(51) Int. Cl.
| | | |
|---|---|---|
| G01T 1/36 | (2006.01) | |
| G01N 23/20 | (2006.01) | |
| G01N 23/207 | (2006.01) | |
| G21K 1/06 | (2006.01) | |

(52) U.S. Cl.
CPC .............. *G01T 1/36* (2013.01); *G01N 23/2076* (2013.01); *G01N 23/20091* (2013.01); *G21K 1/067* (2013.01); *G01N 2223/0568* (2013.01); *H01J 2237/2445* (2013.01); *H01J 2237/24485* (2013.01)

(58) Field of Classification Search
CPC ............ G01N 23/20; G01N 23/20008; G01N 23/2076; G01T 1/36
USPC .................................... 378/70, 82
See application file for complete search history.

(56) References Cited

U.S. PATENT DOCUMENTS 6,259,764 B1    7/2001    Evans-Lutterodt et al.

FOREIGN PATENT DOCUMENTS

| DE | 19542679 | 5/1997 |
|---|---|---|
| DE | 102007048743 | 4/2009 |

*Primary Examiner* — Jurie Yun
(74) *Attorney, Agent, or Firm* — Fox Rothschild LLP (57) ABSTRACT

The present invention relates to a method and device for determining the energetic composition of electromagnetic waves. It is the object of the present invention to provide a method and device for X-ray spectroscopy that allows simultaneous detection of the individual energies at a comparatively higher resolution and/or across a comparatively wider energy range. According to the invention, at least one reflective zone plate (12) is used that comprises a multitude of predefined wavelength-selective regions (14) arranged next to one another, wherein the wavelength-selective regions (14) each include a multitude of reflecting arched portions (20), which extend exclusively and continuously across the respective wavelength-selective region (14).

13 Claims, 7 Drawing Sheets

DEVICE AND METHOD FOR DETERMINING THE ENERGETIC COMPOSITION OF ELECTROMAGNETIC WAVES

CROSS-REFERENCE TO RELATED APPLICATIONS

This application claims priority to and the benefit of German Patent Application No. 10 2013 207 160.4 filed Apr. 19, 2013, titled "DEVICE AND METHOD FOR DETERMINING THE ENERGETIC COMPOSITION OF ELECTROMAGNETIC WAVES," the contents of which are herein incorporated by reference in their entirety.

FIELD OF THE INVENTION

The present invention relates to a method and a device for determining the energetic composition of electromagnetic waves; in particular, this invention relates to a method and device for the simultaneous determination of the energetic composition of electromagnetic radiation from the terrahertz range to the hard X-ray region.

PRIOR ART

Wavelength dispersive spectrometers (WDS) are used to achieve high efficiency and high energy resolutions in X-ray spectroscopy. The radiation is scattered from a lattice or crystal, respectively. Superposition of the scattered rays results in direction-dependent interferences that show wavelength dependence. These interferences are detected by sequentially changing the readout angle. An energy spectrum is successively measured within the focal plane of a refocussing mirror. In total, two or three optical elements are arranged within the device. Energy resolution then is a function of the geometric arrangement (shape of the crystal, aperture slot of the spectrometer) but likewise of the crystal quality, of the optical elements for parallelization and refocussing of radiation and the precision of the spectrometer mechanics. WDS have a considerably better energy resolution than EDS (energy dispersive spectrometers), especially for low energies, but WDS are not suited for a simultaneous measurement of the total spectrum. It is in particular this low-energy region where there is a high line density which requires a good energy resolution for sensitive analyses and clear identification.

Conventionally, natural crystals, diffraction gratings or synthetic layer structures were used for WDS.

The sequential measuring arrangement is quite time-consuming because each element must be approached and analyzed individually. This leads to problems when analyzing unknown samples because it cannot be predicted which elements are present, thus requiring a full spectrum scan. Attempts were made to compensate this measuring time disadvantage by developing multi-channel spectrometers where a limited number of elements are associated with a specific spectrometer. But this is costly and does not provide sufficient flexibility. In addition, these spectrometers have only small acceptance angles, such that only a small portion of radiation coming from the sample is detected and a high excitation intensity must be applied to the sample to achieve sufficient fluorescence intensities.

There is an option to use a von Hamos geometry for spectrometer design in the hard X-ray region (>2100 eV). The radiation from a point source is dispersed by a large crystal. Variation of the angle of incidence of the radiation onto the crystal results in location dependent representation of the spectrum, i.e. the entire spectrum is projected on a line and can be detected simultaneously using a location-dependent detector. Such spectrometers deliver good brilliance. However, the availability of crystals with great lattice constants is limited, which leads to restrictions, especially in the low-energy region, and large expensive crystals and detectors are required to cover a wide energy range. Such spectrometers cannot be used in the soft X-ray region and in the UV range because the HOPG crystals typically used do not have a sufficiently long period.

Furthermore, there are arrangements which generate dispersion using Fresnel zone plates. Fresnel structures create an overlap of phase-offset radiation portions and the resulting interference. The structures used are transmission zone plates, where the phase differences are created by the differences in transmission in these zones. This results in energy-dependent focusing on the zone axis, that is, the spectrum is represented as a function of location along the optical axis of the zone plate.

DE 195 42 679 A1 discloses a method and device for the spectral decomposition and focusing of X-rays wherein the X-rays of a specific energy level are focused on as small a spot on a detector as possible using a reflective zone plate. Focusing on a spot as small as possible is useful for high-resolution detection of emission and absorption lines of an X-ray source and in particular intends to use a planar zone plate, which is less susceptible to tangent errors in angle than a curved zone plate when it comes to achieve a low surface roughness (by polishing).

U.S. Pat. No. 6,259,764 B1 discloses a zone plate with various regions for generating different foci, wherein the various regions are separated from one another.

The arrangements mentioned have the disadvantage that, due to the technological conditions for producing such zone plates, the angle of acceptance is very small, resulting in low spectrometer brilliance, and the efficiency of the zone plates for higher-energy radiation is low because no absorption differences sufficient for high-energy radiation can be produced in the zones. Detection of the spectrum is achieved by moving the detector along the zone plate axis, which means that the spectrum can only be observed sequentially.

DE 10 2007 048 743 B4 discloses a device for spectroscopy that allows simultaneous detection of the individual energy levels at a high resolution across a wide energy range. While the different wavelengths are separated and focused into different regions of the zone plate, the foci of the various wavelengths still are not exactly positioned in the detector plane. Instead, the focus of at most one wavelength is in the detector plane so that the signal for this wavelength can be measured exactly. But the signals of the other wavelengths show considerable "smearing" because the foci are located either before or behind the detector plane. A curved detector, however, would mean considerable extra expenditure. Because of the disadvantages mentioned, the resolution and the width of the measurable energy range are limited, since the distance of the focus from the detector plane corresponds to the energetic distance of the detected wavelength from that wavelength to the focus of which the detector plane was set.

According to DE 195 42 679 A1, a reflective zone plate is used of which only an off-axis section is used. The radiation from the source is focused into a spot with small-dimensions using an elliptical diffraction structure. The wave dispersion in the diffraction plane is used for measuring the spectrum. The disadvantage of this solution is the relatively small measuring range for the energy (<5%) due to smearing of the focal spot by diffraction (chromatic absorption) for energies outside the central region.

DISCLOSURE OF THE INVENTION

It is therefore the object of the present invention to provide a method and device for spectroscopy, in particular, for X-ray spectroscopy, that allows simultaneous detection of individual energies at a comparatively higher resolution, higher light intensity, and/or across a comparatively wider energy range. Another object of this invention is the ability to detect the X-ray radiation spectrum fast, at a high resolution, and with cost-efficient components.

These objects are achieved according to the invention by a device having the characteristics listed in claim 1. Preferred embodiments of the invention are contained in the dependent claims.

The device according to the invention offers the particular advantage that it allows simultaneous detection at a higher spectral resolution and greater width of the measurable energy range. This avoids sequential reading out of each wavelength region so that measurements can be performed faster and all elements located in the respective energy range can be detected. It is also possible to focus the radiation of different wavelengths into different receiving sections of the detector plane at high imaging quality, which allows a considerable increase in spectral resolution due to the small focus diameter that can be achieved in the detector plane.

According to an aspect of the invention, a device is disclosed for determining a spectrum of electromagnetic waves from a source, comprising: at least one reflective zone plate and at least one position-resolving detector, wherein the reflective zone plate comprises a multitude of predefined, wavelength-selective regions arranged next to one another and the position-resolving detector comprises a multitude of corresponding receiving sections, wherein the wavelength-selective regions each include a multitude of reflecting arched portions which exclusively (and preferably continuously) extend across the respective wavelength-selective region.

Preferably the arched portions each form a part of an ellipse and extend along at least 1% of the circumference of the respective ellipse, even more preferred, the arched portions extend along at least 10% of the circumference of the respective ellipse.

Since the reflecting arched portions extend exclusively across the respective wavelength-selective region providing spatial and energetic spaces the wavelength-selective regions can be designed such that focusing is not just performed transversely to the propagation direction of the electromagnetic wave for each wavelength, but the position of the focus is set such that the foci of all wavelengths are located in the detector plane. In this case, the energy resolution is defined by the energy gap between the arched portions and the size of the pixels of the detector.

A reflective zone plate where the reflecting arched portions extend continuously across all wavelength-selective regions (DE 10 2007 048 743 B4) may be suitable to separate the wavelength but will not be able to position each focus in a detector plane. With other words, according to the invention a multi-channel analyzer is disclosed, while a continuously functioning spectrometer is described in DE 10 2007 048 743 B4. Due to the separate channels for the individual elements or energies according to the invention, the signal-/ground ratio is increased compared to the solution mentioned before. The technology for the production of discrete channel structures advantageously is also cheaper than the technology for the production of continuous structures, since the dimensions of the elements (elliptical portions) of the continuous structures are by far smaller. Larger structural elements have a by far higher diffraction efficiency (up to a factor of 10) and improve the characteristics of the spectrometer. Due to the discrete channels, a further optimization between the Fresnel spectrometer and the detector is possible, so every focusing channel can be aligned to one pixel of the detector respectively.

Preferably, the elliptically formed portions each have (preferably exactly) one main peak. Preferably, the main peaks are turned away from the detector respectively. Alternatively the main peaks are turned towards the detector respectively. This depends on the diffractive order.

Preferably, the main peaks of all the portions of a respective wavelength-selective region are arranged along a line (the so-called second axis). Preferably, the tangents to the main peak points of all portions of a respective wavelength-selective region are arranged in parallel to each other respectively. Preferably, all portions of a respective wavelength-selective region are arranged spaced from each other.

Preferably, the number of wavelength-selective regions is determined by the number of pixels on the horizontal line within the detector plane, where the focal points of the Fresnel spectrometer are positioned. For example given a detector with 2000 pixels on that line, it is possible to produce 2000 elliptical portions. Preferably, the multitude of wavelength-selective regions is separately arranged adjoining one another, so the elliptical portions of neighboring wavelength-selective regions do not continuously merge. It is especially preferred, that the elliptical portions of neighboring wavelength-selective regions are spaced from each other.

Preferably, the multitude of elliptically formed portions of a respective wavelength-selective region is arranged separately and spaced from each other. Preferably, the wavelength-selective regions extend along a first axis (side by side), while the elliptically formed portions (of the respective wavelength-selective region) extend along a second axis (so one above the other related to FIGS. 2a and 2b), wherein the second axis is perpendicular to the first axis.

Preferably, the second axes of neighboring wavelength-selective regions enclose an angle which is greater than zero. Preferably, this angle is smaller than 15°, preferably smaller than 10° and even more preferred smaller than 5°.

The total angle enclosed between the first elliptical portion and the last elliptical portion is determined by the dimension of the detector. Preferably, the elliptically formed portions of the wavelength-selective regions are each formed symmetrically to a line which is perpendicular to a tangent at the respective main peak point.

Preferably, the elliptically formed portions extend along at least 15% of the circumference, even more preferred along at least 20% of the circumference, even more preferred along at least 25% of the circumference, even more preferred along at least 30% of the circumference, even more preferred along at least 35% of the circumference, even more preferred along at least 40% of the circumference and even more preferred along at least 45% of the circumference of the respective ellipse.

It is especially preferred that the elliptically formed portions extend along at least 50% of the circumference of the respective ellipse.

Preferably, the elliptically formed portions of the wavelength-selective regions are almost equidistantly spaced to each other respectively, so that the ratio of the distance between two neighboring elliptically formed portions (of a wavelength-selective region) to the distance between the respective adjacent neighboring elliptically formed portions has a value between 0.9 and 1.1. Preferably, all elliptically formed portions (of a wavelength-selective region) have the same orientation, so they are congruent to each other (or rather the tangents at the respective main peak points are parallel), whereas the elliptically formed portions of different (e.g. neighboring) wavelength-selective regions enclose a finite angle.

Preferably, the maximum curvature of the elliptically formed portions is between r=10 mm and r=40 mm. Preferably, the minimum curvature of the elliptically formed portions is between r=10 µm and r=1 mm.

The factor $$\frac{1}{r} = \frac{\Delta\varphi}{\Delta s},$$

which is the ratio of an angle at center of an arc of circle to the length of the arc of circle, serves as a measure for the curvature of a circle. The angle at center is equal to the angle which is enclosed between the tangents to the circle at the endpoints of the arc of circle. In order to define the curvature of an arbitrary curve in a point, a respective curve piece of the length Δs which contains the certain point and which has tangents at its end points that intersect in an angle Δφ is considered. It is preferred that a multitude of reflecting (particularly preferably elliptical) wavelength-selective regions (which are particularly preferably designed as Fresnel zone plates) are arranged in fan-like manner next to one another, wherein a central energy of at least one of the wavelength-selective regions (preferably of a multitude of wavelength-selective regions, particularly preferably of all wavelength-selective regions) differs only slightly (less than 10%, more preferred less than 5%, more preferred less than 3%, even more preferred less than 1% and even more preferred less than 0.5%) from the central energy of the respective neighboring wavelength-selective region or neighboring wavelength-selective regions. It is preferred that a central energy of at least one of the wavelength-selective regions (preferably of a multitude of wavelength-selective regions, particularly preferably of all wavelength-selective regions) differs from the central energy of the respective neighboring wavelength-selective region or neighboring wavelength-selective regions In this way, the measuring range for the energies to be examined can be increased more than tenfold.

In an alternative preferred embodiment, not all wavelength-selective regions comprise a slightly different central energy but a multitude of identical wavelength-selective regions are arranged separately next to one another for at least one energy value. This allows a further increase of the imaging aperture for this energy value. A prerequisite for determining a spectrum is, however, that at least a multitude of wavelength-selective regions with different central energies are integrated on the reflective zone plate whose (neighboring) central energies differ only slightly from one another.

It is preferred that neighboring wavelength-selective regions are directly adjacent. An accompanying advantage is that a large number of wavelength-selective regions can be provided on a reflective zone plate, resulting in a particularly high spectral resolution or a comparatively wider energy range.

The arched portions preferably comprise webs with a planar top surface while grooves are provided between the arched portions. It is particularly preferred that the zone plate is made in one piece. The grooves then form the non-reflective regions (given an advantageous angle of incidence) whereas the webs of the zone plate, which are positioned higher relative to the grooves, form the reflective (arched) portions.

The depth of the grooves between neighboring arched portions (of one, preferably of each, wavelength-selective region) preferably increases continuously in the direction towards the detector. An accompanying advantage is that this design allows a particularly high spectral resolution or particularly good focusing of the radiation of all wavelengths into the respective receiving sections.

The distance of neighboring portions (of one, preferably of each, wavelength-selective region) along the longitudinal extension of the portions from a first end of the neighboring portions to a second end of the neighboring portions changes continuously in accordance with the Fresnel relationship.

The distance of neighboring portions (of one, preferably of each, wavelength-selective region) along an axis perpendicular to the longitudinal extension of the portions from an end of the zone plate facing away from the detector to an end of the zone plate facing the detector changes continuously in accordance with the Fresnel relationship.

The reflecting portions (of one, preferably of each, wavelength-selective region) preferably comprise a curvature in accordance with the wavelength range to be measured and the geometric dimensions and distances of source, zone plate, and detector.

The arched portions of all wavelength-selective regions are preferably shaped such that the electromagnetic waves of the incident polychromatic radiation are focused into a multitude of detector sections, which are arranged along a line.

The active surface of the detector preferably has a planar design. If required, the detector may also be tilted. The multitude of corresponding receiving sections is preferably arranged along a line on the detector. A connecting line between the source and a centrally positioned wavelength-selective region on the zone plate and a line on which the receiving sections are arranged preferably enclose an angle between 70° and 110°, more preferably between 80° and 100°, even more preferably between 85° and 95°, and even more preferably an angle of 90°.

The device is preferably used for determining the energetic composition of electromagnetic waves in the range from 10 to 2000 eV, more preferably from 150 to 1000 eV.

The reflective structures are preferably formed by webs between 1 nm and 100 nm in height, more preferably between 5 nm and 40 nm in height, and/or the width of these structures is between 0.1 µm and 10 µm, more preferably between 0.5 µm and 4 µm.

All receiving sections are preferably arranged along a line that extends parallel to the surface of the carrier substrate.

The device preferably comprises means for detecting and calculating the spectrum (energetic distribution) of the X-rays of the source from the simultaneously detected intensities of at least two receiving sections.

In another preferred embodiment of the invention, at least one other (second) reflective zone plate is provided, wherein the first reflective zone plate and the second reflective zone plate are arranged relative to one another such that the X-ray radiation they reflect and diffract is focused in a way that the respective focal points or focal areas impinge on a joint position-resolving detector (spatially separated with respect to varying energy levels of the radiation). The first reflective zone plate and the second reflective zone plate are preferably arranged in parallel to one another (one on top of the other or one behind the other). The second zone plate preferably also comprises a carrier substrate with a planar top surface and reflective structures located on the top surface of the carrier substrate, wherein the structures of the first reflective zone plate and the structures of the second reflective zone plate are dimensioned such that different wavelengths (wavelength ranges) or energies, respectively, of the electromagnetic radiation are focused on the detector (or respective detectors).

According to another aspect of the invention, a reflective zone plate for focusing and selecting the wavelengths of the electromagnetic waves is disclosed, comprising: a multitude of predefined, wavelength-selective regions arranged next to one another, and the position-resolving detector comprises a multitude of corresponding receiving sections, wherein the wavelength-selective regions each include a multitude of reflecting arched portions which exclusively and continuously extend across the respective wavelength-selective region.

It is preferred that the multitude of wavelength-selective regions are arranged separately and next to one another.

It is preferred that neighboring wavelength-selective regions are directly adjacent. An accompanying advantage is that a large number of wavelength-selective regions can be provided on a reflective zone plate, resulting in a particularly high spectral resolution or an accordingly wider energy range.

The arched portions preferably comprise a planar top surface while grooves are provided between the arched portions. It is particularly preferred that the zone plate is made in one piece. The grooves then form the non-reflective regions (given an advantageous angle of incidence) whereas the areas of the zone plate, which are positioned higher relative to the grooves, form the reflective (arched) portions.

The depth of the grooves (or the height of the webs, respectively) between neighboring arched portions (of one, preferably of each, wavelength-selective region) preferably changes (increases or decreases) continuously in a first direction extending perpendicular to the longitudinal extension of the portions. An accompanying advantage is that this design allows a particularly high spectral resolution or particularly good focusing of the radiation of all wavelengths into the respective receiving sections, respectively.

The distance of neighboring portions (of one, preferably of each, wavelength-selective region) along the longitudinal extension of the portions from a first end of the neighboring portions to a second end of the neighboring portions changes continuously in accordance with the Fresnel relationship.

The distance of neighboring portions (of one, preferably of each, wavelength-selective region) along an axis perpendicular to the longitudinal extension of the portions from a first end of the zone plate to a second end of the zone plate changes continuously in accordance with the Fresnel relationship.

The device is preferably used for generating a spectrum of electromagnetic waves in the range from 10 to 2000 eV, more preferably from 150 to 1000 eV.

According to another aspect of the invention, a method for determining the energetic composition of electromagnetic waves, in particular, of X-ray radiation from a source, is disclosed that comprises the following process steps:
Irradiation of a reflective zone plate with the polychromatic electromagnetic radiation from the source, wherein
at least two different wavelength ranges of the irradiated X-rays are reflected and diffracted by predefined wavelength-selective regions of the reflective zone plate that are arranged next to one another and focused into predefined receiving sections that are separate from one another and located in one plane, and
detection of the X-ray radiation reflected and diffracted from the zone plate in the at least two receiving sections, wherein the reflected and/or diffracted electromagnetic radiation of different wavelengths is focused by means of a multitude of separate wavelength-selective regions, each of which including a multitude of reflecting arched portions which exclusively and continuously extend across the respective wavelength-selective region, into different focal points or focal areas such that the respective focal points or focal area are arranged along a line in the plane of the receiving sections, and the longitudinal axis of the line formed by the respective focal points or focal areas is perpendicular or substantially perpendicular to the diffraction direction of the wavelength-selective regions, and the energetic composition of the electromagnetic radiation of the source is determined from the simultaneously detected intensities of the at least two receiving sections.

The source in the meaning of the invention can be a primary source of electromagnetic radiation (preferably X-ray radiation) but also a test specimen that emits, reflects, and/or absorbs electromagnetic radiation (for example in absorption spectroscopy).

According to the invention, electromagnetic radiation is focused depending on its wavelength (energy) into a multitude of sections arranged next to one another using the reflective (Fresnel) zone plate, such that the different energies impinge on different spots of a position-resolving detector (which may also be comprised of several detectors) and the spectrum or the energetic composition can be deduced from the measured values of the position-resolving detector (or the individual detectors, respectively).

The polychromatic X-ray radiation is preferably directed onto the reflective zone plate at an angle of incidence between 0.05° and 5°, more preferably between 1° and 3°. The reflective zone plate is preferably positioned at a distance between 5 mm and 50 mm from the source and/or the receiving sections are positioned at comparable distances from the reflective zone plate. The distances depend on the desired energy resolution and the detector size. The Fresnel structure can be calculated accordingly.

According to the invention, the reflected and/or diffracted X-ray radiation of different wavelengths is focused into different focal points or focal areas using the wavelength-selective regions such that the respective focal points or focal areas are arranged along a line in the plane of the receiving sections, wherein the longitudinal axis of the line formed by the respective focal points or focal areas is perpendicular or substantially perpendicular to the diffraction direction of the wavelength-selective regions. In the case of focal areas, the line is determined by the geometric center of the focal areas.

The incident X-ray radiation is preferably focused into separate focal points or focal areas depending on the wavelength of the X-ray radiation by means of a multitude of reflecting portions (shaped as arched portions with preferably linear edges, the curvature of which is continuously changing). The wavelength-selective regions are preferably arranged next to one another on the zone plate with respect to the propagation direction of the X-ray radiation.

The polychromatic X-ray radiation from the source is preferably incident on a first reflective zone plate and at least one second reflective zone plate, and the X-ray radiation reflected and diffracted from the zone plates is detected in the at least two receiving sections. This makes it possible to a resolve a separate energy range very highly with each zone plate and measure it at the same time; these energy ranges may be adjoining or overlapping. The first reflective zone plate and the second reflective zone plate are preferably positioned relative to one another such that the X-ray radiation is focused in a way that the respective focal points or focal areas impinge onto a joint position-resolving detector.

For detecting trace elements, a parallel arrangement is particularly suitable to increase the aperture angle and thus the light intensity of the spectrometer.

In accordance with another aspect of the invention, the device is characterized in that it is used in combination with a linear array or area detector in a scanning electron microscope.

In accordance with another aspect of the invention, the device is characterized in that it is used in combination with a linear array or area detector in a transmission electron microscope.

In accordance with another aspect of the invention, the device is characterized in that it is used in combination with a linear array or area detector in a Synchrotron beam line.

In accordance with another aspect of the invention, the device is characterized in that it is used in combination with a linear array or area detector as a wavelength-dispersive X-ray spectrometer in a particle-induced x-ray emission system (PIXE emission system).

BRIEF DESCRIPTION OF THE DRAWINGS

The invention will be explained in greater detail with reference to exemplary embodiments below. Wherein:

FIG. 2a: shows a detailed schematic top view of a device according to the invention according to FIG. 1a;

DETAILED DESCRIPTION OF THE INVENTION

Figure 1A:
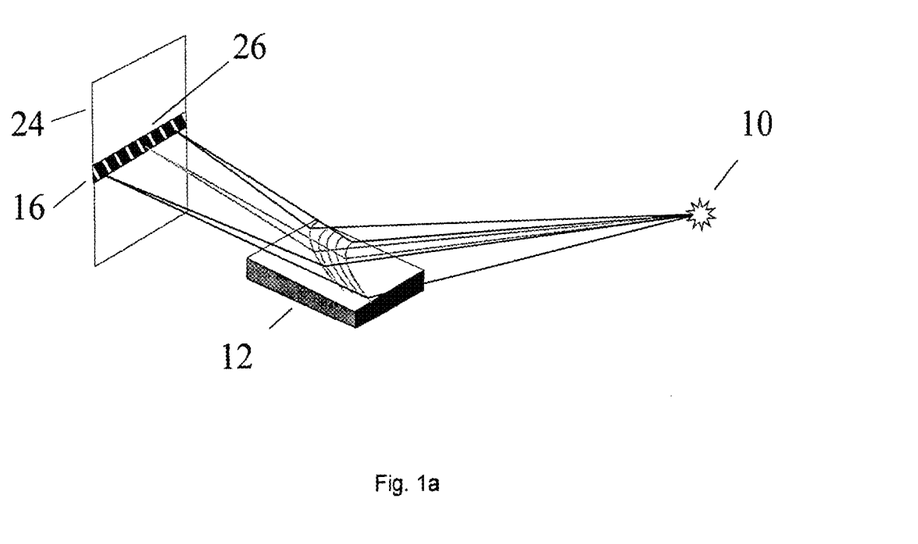
FIG. 1a: shows a schematic perspective view of a device according to the invention for X-ray spectroscopy according to a first embodiment with a zone plate comprising a carrier substrate with a planar surface.

FIG. 1a shows a schematic perspective view of a preferred embodiment of the device according to the invention. In order to determine the energetic composition of electromagnetic radiation (preferably X-ray radiation) of the X-ray radiation source 10, the X-ray radiation originating from this radiation source 10 irradiates, according to the invention, the reflective zone plate 12, wherein the reflective zone plate 12 is designed such that X-ray radiation of a specific wavelength range is focused into a predefined detector section of the position-resolving detector 16. The surface of the zone plate 12 is even (planar) according to the embodiment shown in FIG. 1a. This evenness however does not refer to the reflecting lines or webs 20 (see FIGS. 3 and 4) but to the surface of the carrier substrate 18 of the zone plate 12. In an alternative embodiment (FIG. 1b), the surface of the carrier substrate 18 of the zone plate 12 is curved (concave) on the inside. Use of a curved zone plate 12 can increase the light intensity in the detector 16; however, producing such a curved zone plate 12 (FIG. 1b) requires a considerably greater production effort than producing a zone plate with a planar carrier substrate. The curvature of the zone plate 12 is adjusted to the respective geometrical conditions (i.e. the distance of the X-ray source 10 to the zone plate 12 or to individual regions 14 and the distance of said regions 14 to the detector sections 22 and the respective angles) for achieving maximum light intensity in the detector sections 22.

Figure 1B:
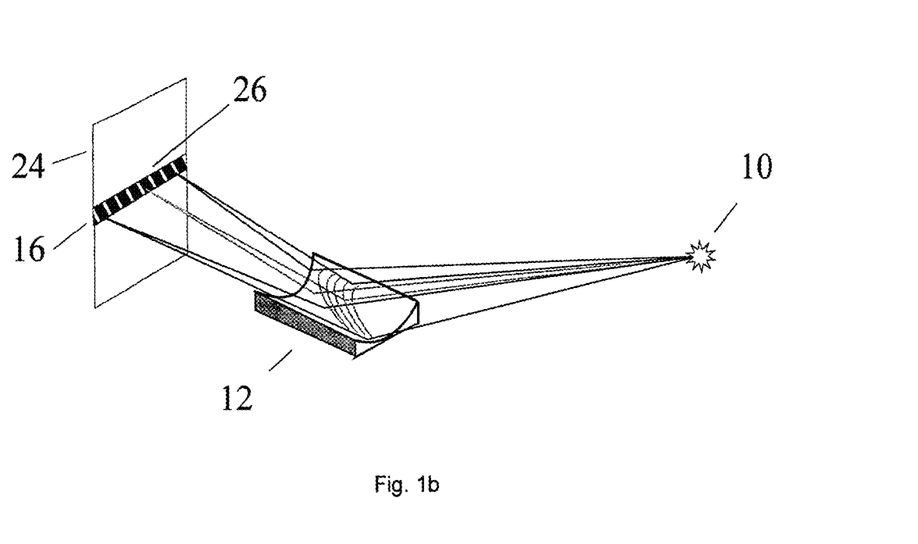
FIG. 1b: shows a schematic perspective view of a device according to the invention for X-ray spectroscopy according to a second embodiment with a zone plate comprising a carrier substrate with a curved surface.

The detector 16 has a slit aperture 26 located in the focal plane of the zone plate 12 in front of the detector 16 that keeps scattered, non-focused light from being detected. An alternative solution to using a slit aperture 26 is a design in which only the focal area of the detector 16 is read out, which would eliminate the need for a slit aperture 26.

Since only a schematic top view is shown in FIGS. 1a and 1b, the reflective regions are shown as being continuously spread over the zone plate 12 for reasons of clarity, even though these reflective regions are exclusively arranged continuously within the respective separate wavelength-selective regions 14 and in fact are designed discontinuously in between neighboring wavelength-selective regions 14 according to the invention. (FIGS. 2a and 2b)

Figure 2A:
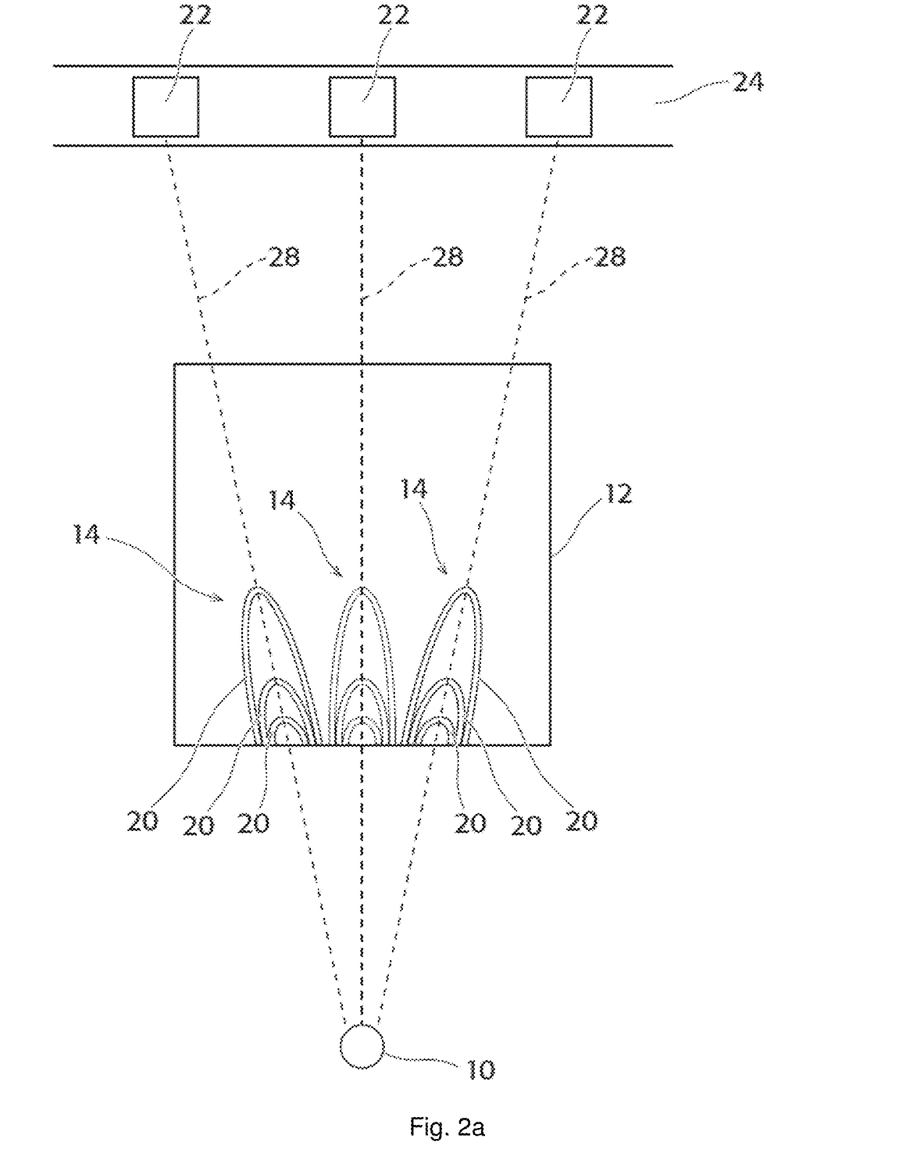
Figure 2B:
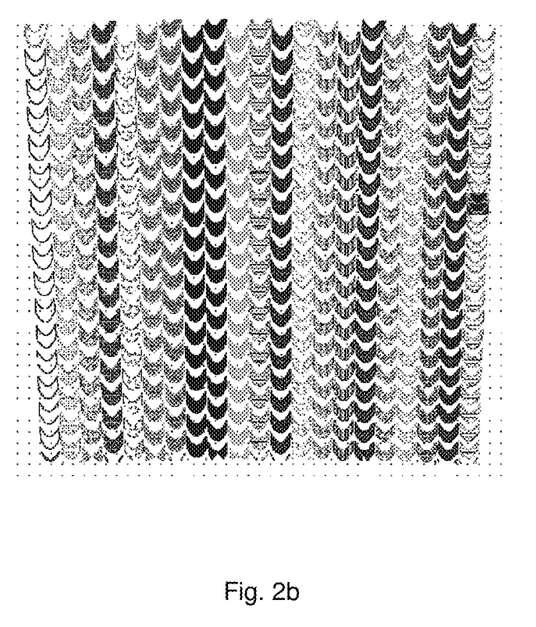
FIG. 2b: shows a detailed schematic top view of a device according to the invention and according to a further preferred embodiment.

The zone plate 12 according to the invention is designed to focus different wavelengths into different detector sections 22 (FIG. 2a). In this way, the wavelength-dispersive system can detect the split X-ray radiation simultaneously across a wide energy range. Linear arrays of photodiodes, CCD, or position-resolving proportional counters can be used as detectors. Each region 14 of the zone plate 12 must be designed for a different energy level to achieve dispersion of the radiation along the detector 16 into detector sections 22 (see FIG. 2a) and generate a continuous image of the spectrum. The detector system must be adjusted to the energy resolution and to the energy range to be detected. The embodiment can cover an energy range of 500 eV (e.g. between 500 and 1000 eV) at a resolution of about 10 eV (for a detector with 100 channels). The zone plate 12 is for this purpose adjusted to the respective geometrical conditions (i.e. the distance of the X-ray source 10 to the zone plate 12 or to individual regions 14 and the distance of said regions 14 to the detector sections 22 and the respective angles) for achieving maximum light intensity in the detector sections 22. According to the embodiment of FIG. 2a, the main peaks are turned away from the detector 22 respectively. According to the embodiment of FIG. 2b, the main peaks are turned towards the detector 22 respectively.

Unlike the zone plate disclosed in DE 10 2007 048 743 B4 in which the reflective portions (webs) extend continuously across all wavelength-selective regions 14, the reflecting arched portions 20 according to this invention, while also extending continuously, only (exclusively) extend across the respective wavelength-selective region. In other words, arched portions 20 of a wavelength-selective region 14 do not continuously merge into an arched section 20 of a neighboring wavelength-selective region 14. This increases the spectral resolution because the foci are better focused in the detector plane. While the zone plate disclosed in DE 10 2007 048 743 B4 allows the radiation to be focused in one direction (transversely to the propagation direction), the separate arched portions 20 of different regions 14 allow focusing of the radiation in two directions.

Instead of using an off-axis zone plate as in DE 195 42 679 A1, a multitude of reflective elliptical Fresnel zone plates are arranged next to one another in a fan-like fashion to extend the measuring range for the energies to be examined, wherein the central energy of at least one of the zone plates (preferably a multitude of zone plates, particularly preferably all zone plates) differs only slightly (less than 10%, more preferably less than 5%, more preferably less than 3%, even more preferably less than 1% and even more preferably less than 0.5%) from the central energy of the respective other (at least one, optionally two) neighboring zone plate(s). In this way, wave dispersion synthetically generated in a plane perpendicular to the diffraction plane allows a more than tenfold increase of the measuring range for the energies to be examined. The option to use the dispersion in the diffraction plane for obtaining a high energy resolution remains unaffected.

Figure 3:
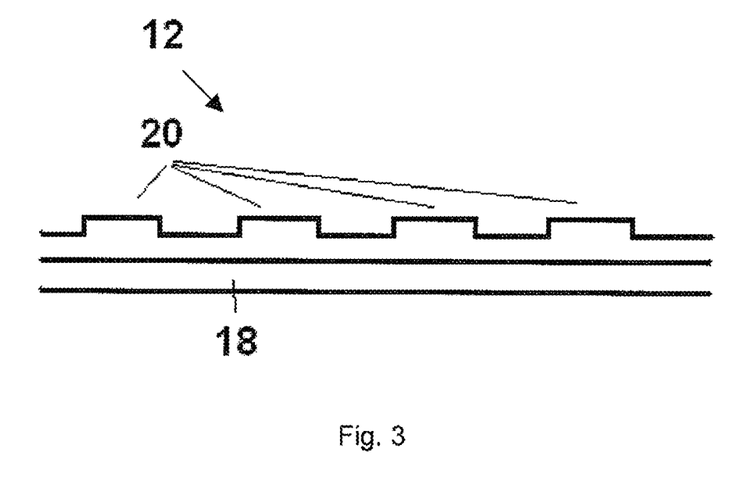
FIG. 3: shows a schematic sectional view of the reflective zone plate used in the device according to the invention.
Figure 4:
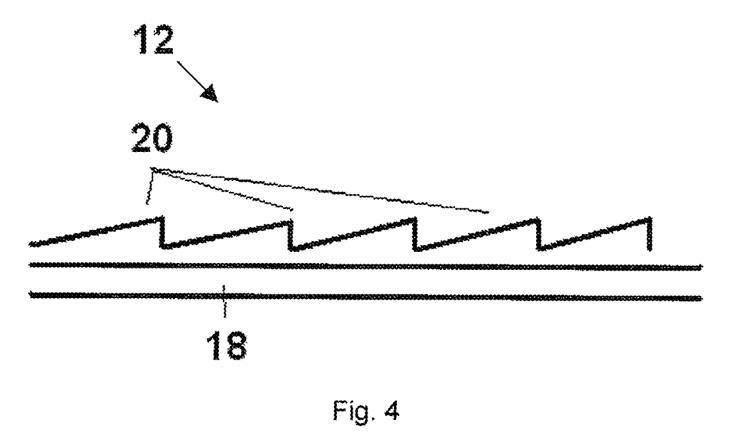
FIG. 4: shows a schematic sectional view of an alternative embodiment of the reflective zone plate used in the device according to the invention with Blaze array.

FIGS. 3 and 4 show a schematic view of a cross section of the zone plate 12 used here. The reflective zone plate 12 may consist of a substrate 18 (such as a super polished Si wafer 18 with metallic reflective structures 20, e.g. gold or silver). The respective structures 20 on the surface can for example be produced on the surface 18 by etching and/or depositing. As is apparent from FIGS. 1a and 1b, it is particularly preferred that the reflecting structures 20 for the different regions 14 continuously blend into one another (FIG. 2a) so that a continuous spectrum of the X-ray radiation of the source 10 can be measured along the line of the detector 16. Energy resolution is determined by the number of channels of the detector 16 along the lines formed by the focal points (also for each wavelength) and the precision of the structures. In this embodiment, a detector 16 was used with a length of 25 mm and a resolution of 1024 channels. The measured signals of each channel can be adjusted using respective detection efficiency curves. The device according to the invention is to be used, in particular, for detecting low-energy X-ray radiation up to 4 keV. FIG. 4 shows a Blaze structure which can also be used for generating the phase differences.

The representation of the spectrum can be at a scale of 1:1 but also scaled up or down using such an arrangement according to the invention. This provides options for adjusting the energy resolution and geometry to the respective application, so that detectors of predefined sizes (pixel size and number of pixels) can be used.

Figure 5:
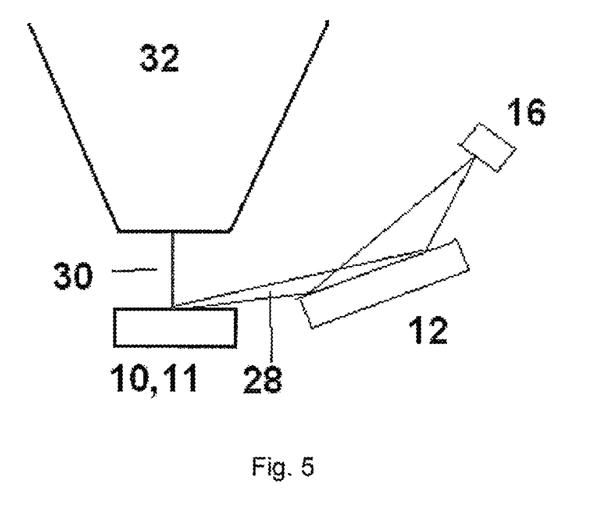
FIG. 5: shows the use of the device according to the invention for X-ray fluorescence spectroscopy in a scanning electron microscope.

FIG. 5 shows the use of the device according to the invention for X-ray fluorescence spectroscopy in a scanning electron microscope. The specimen 11 is excited to fluoresce and thus to emit X-rays by the electron beam 30 of an electron microscope (the reference symbol 32 refers to the pole piece of the electron microscope here) and thus becomes the source 10 for X-ray spectroscopy. The polychromatic X-ray radiation 28 emitted by the specimen 11 is now projected onto the detector 16 by the reflective zone plate 12, wherein the X-ray radiation can be focused into different sections 22 of the detector 16 depending on its energy as shown in FIG. 1a (and FIG. 1b) and thus detected separately, allowing simultaneous detection of the spectrum of the X-ray radiation emitted by the specimen 11. Protons, α particles or ions may also be used for exciting fluorescence.

Figure 6:
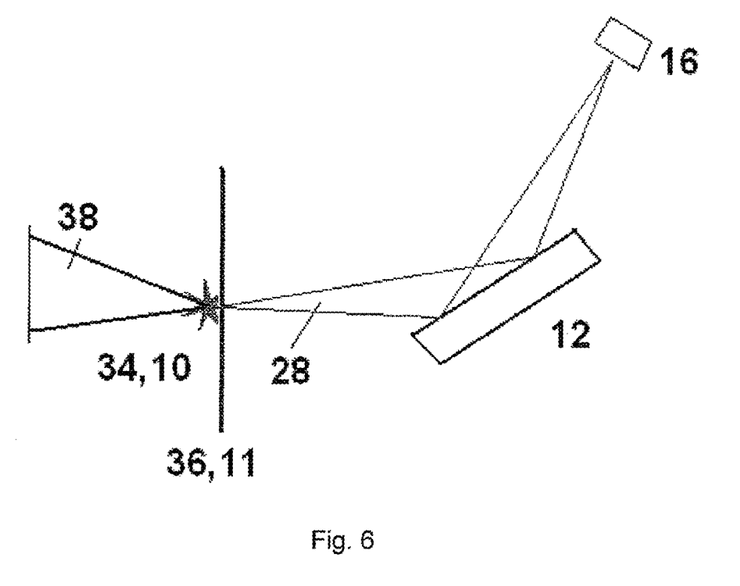
FIG. 6: shows the use of the device according to the invention for simultaneous broadband characterization of short-time plasma sources.

FIG. 6 shows the use of the device according to the invention for simultaneous broadband characterization of short-time plasma sources. The radiation 38 of a pump laser (excitation radiation) is focused onto a target material 36, which excites a plasma 34 that is used as the source 10 of the X-ray radiation. The X-ray radiation 28 emitted by the plasma 34 is now directed via the reflective zone plate 12 onto the detector 16 and focused (position-resolved) into different sections 22 of the detector 16 (see FIGS. 1a, 1b, 2a and 2b) such that the energetic composition of the polychromatic X-ray radiation 28 of the plasma 34 can be determined.

Figure 7:
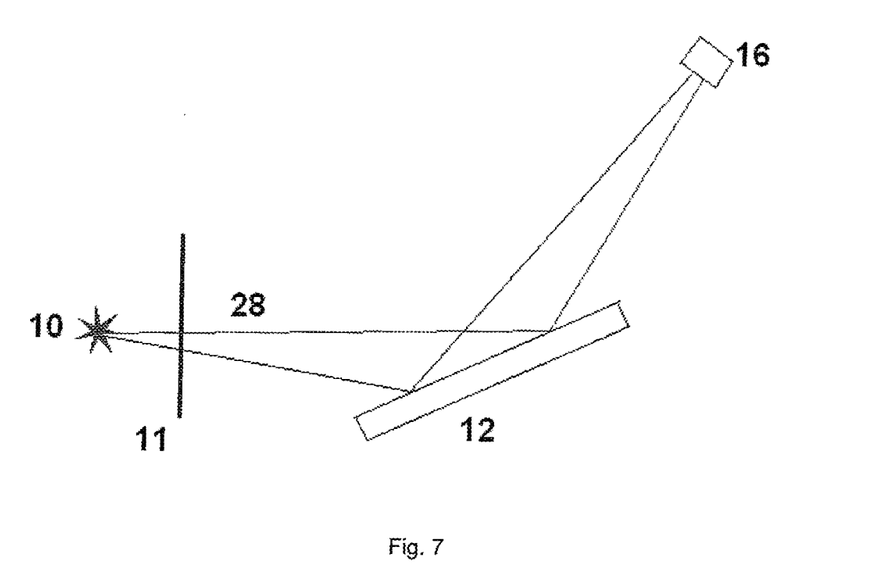
FIG. 7: shows the use of the device according to the invention for position-dependent and high-resolution measurement of X-ray absorption spectra.

FIG. 7 is a schematic view of the use of the device according to the invention for high-resolution absorption spectroscopy. A specimen 11 is irradiated with the X-ray radiation of an X-ray source 10, wherein the X-rays emitted by the X-ray radiation source 10 are partially absorbed by the specimen 11, such that conclusions about the specimen 11 can be drawn from the detected spectrum. The X-ray radiation 28 modified by the specimen 11 is now once again directed via the reflective zone plate 12 onto the position-resolving detector 16 and focused into different sections depending on their wavelengths (see FIGS. 1a, 1b, 2a and 2b) such that the absorption spectrum of the specimen 11 can be determined.

Figure 8:
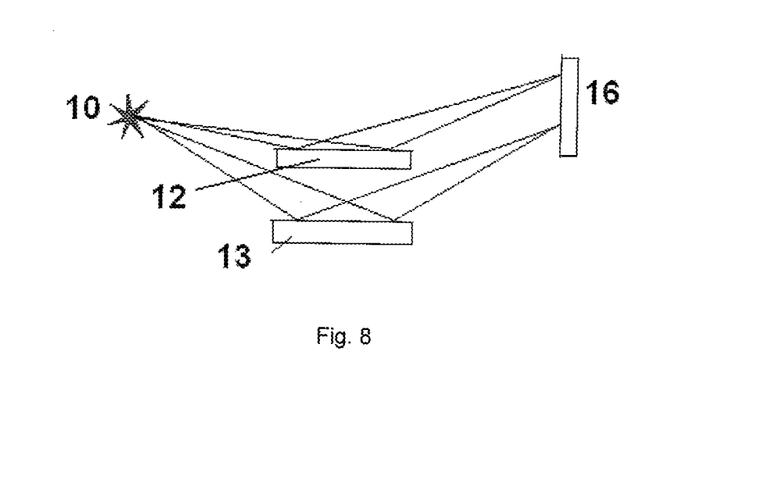
FIG. 8: shows another embodiment of the device according to the invention with two reflective zone plates arranged one on top of the other.
Figure 9:
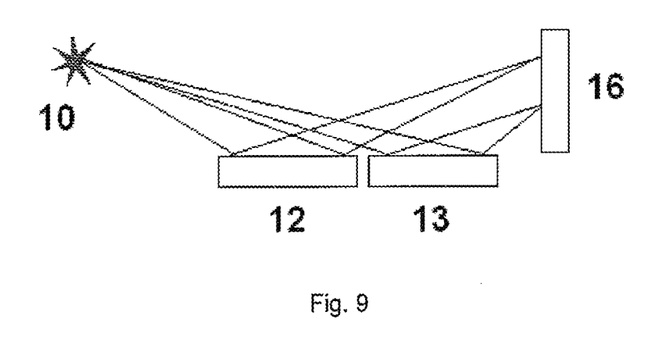
FIG. 9: shows an alternative embodiment of the device according to the invention with two reflective zone plates arranged next to one another.

FIGS. 8 and 9 each show another preferred embodiment of the invention, wherein a first reflective zone plate 12 and a second reflective zone plate 13, which are configured for different energy ranges, are arranged such that the X-ray radiation of the source 10 is directed both via the first reflective zone plate 12 and the second reflective zone plate 13 onto a detector 16 or a multitude of detectors. The reflective zone plates 12 and 13 are preferably configured for different, non-overlapping energy ranges, i.e. the reflective zone plate 12 focuses X-ray radiation onto the detector 16 that is different in wavelength from the X-ray radiation which the reflective zone plate 13 focuses onto the detector. This preferred embodiment allows simultaneous detection of particularly great energy ranges.

As shown in FIGS. 8 and 9, the two zone plates 12, 13 can be arranged one on top of the other or next to one another, for example.

Figure 10:
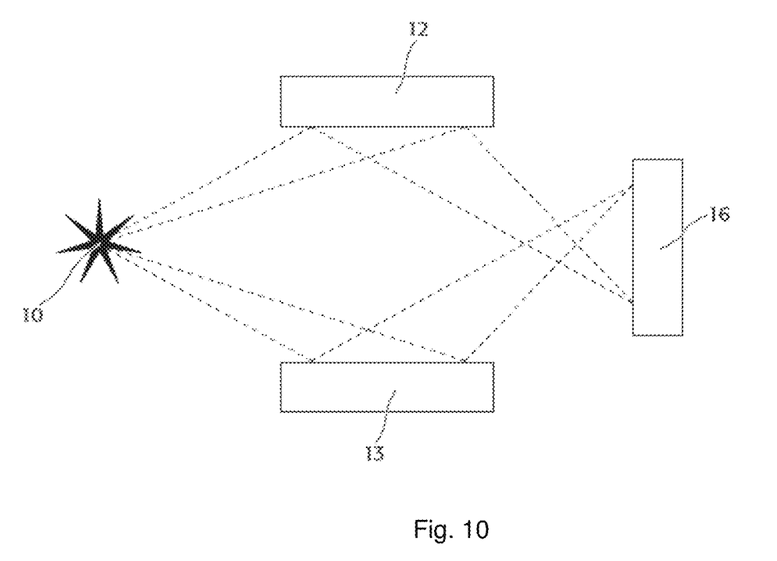
FIG. 10: shows an alternative embodiment of the device according to the invention with two reflective zone plates arranged opposite one another.

FIG. 10 shows an arrangement of opposite zone plates 12, 13 which have a different or the same configuration. In the first case, different energy ranges can be detected, or the second zone plate may have a greater aperture for selected energies. In the second case, the intensities associated with an energy could be added in the two activated pixels, which would increase the signal strength.

LIST OF REFERENCE SYMBOLS

10 Source
12 Zone plate
14 Wavelength-selective region
16 Position-resolving detector
20 Reflecting arched portion
22 Receiving sections of the detector
26 Slit aperture
28 Connecting line between source and detector

The invention claimed is:

1. A device for determining a spectrum of electromagnetic waves of a source, comprising:
at least one reflective zone plate and at least one position-resolving detector, wherein the reflective zone plate comprises a multitude of predefined wavelength-selective regions arranged next to one another and the position-resolving detector comprises a multitude of corresponding receiving sections,
wherein the wavelength-selective regions each include a multitude of reflecting arched portions which exclusively extend across the respective wavelength-selective region, characterized in that the arched portions each form a part of an ellipse, wherein the arched portions extend along at least 10% of the circumference of the respective ellipse.

2. The device according to claim 1, wherein the multitude of wavelength-selective regions are arranged separately next to one another.

3. The device according to claim 1, wherein a multitude of identical wavelength-selective regions are arranged separately next to one another.

4. The device according to claim 1, wherein a central energy of at least one of the wavelength-selective regions differs by less than 10% from a central energy of a neighboring wavelength-selective region.

5. The device according to claim 4, wherein a central energy of a multitude of wavelength-selective regions differs by less than 1% from a central energy of the respective neighboring wavelength-selective region.

6. The device according to claim 5, wherein a central energy of each of the wavelength-selective regions differs by less than 1% from a central energy of the respective neighboring wavelength-selective region.

7. The device according to claim 1, wherein neighboring wavelength-selective regions are adjacent to one another.

8. The device according to claim 1, wherein the arched portions preferably comprise a planar top surface while grooves are provided between the arched portions.

9. The device according to claim 8, wherein a depth of the grooves between neighboring arched portions increases continuously in the direction towards the detector.

10. The device according to claim 1, wherein a distance of neighboring portions along a longitudinal extension of the portions from a first end of the neighboring portions to a second end of the neighboring portions changes continuously in accordance with the Fresnel relationship.

11. The device according to claim 1, wherein a distance of neighboring portions along an axis perpendicular to a longitudinal extension of the portions from an end of the zone plate facing away from the detector to an end of the zone plate facing the detector changes continuously in accordance with the Fresnel relationship.

12. The device according to claim 1, wherein the reflecting portions preferably comprise a curvature in accordance with a wavelength range to be measured and the geometric dimensions and distances of source, zone plate, and detector.

13. The device according to claim 1, wherein the detector is planar and/or the multitude of corresponding receiving sections are arranged along one line.

* * * * *